US00PP25706P2

(12) United States Plant Patent
Pounders et al.

(10) Patent No.: US PP25,706 P2
(45) Date of Patent: Jul. 14, 2015

(54) AZALEA PLANT NAMED 'AZ 32'

(50) Latin Name: *Rhododendron hybrida*
Varietal Denomination: AZ 32

(71) Applicants: The United States of America, as represented by the Secretary of Agriculture, Washington, DC (US); Capstone Plants Inc., Grand Saline, TX (US)

(72) Inventors: Cecil T Pounders, Poplarville, MS (US); James B Berry, Mineola, TX (US)

(73) Assignees: CAPSTONE PLANT, INC., Grand Saline, TX (US); THE UNITED STATES OF AMERICA AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 175 days.

(21) Appl. No.: 13/987,578

(22) Filed: Aug. 9, 2013

(51) Int. Cl.
*A01H 5/00* (2006.01)

(52) U.S. Cl.
USPC ..... Plt./240

(58) Field of Classification Search
USPC ..... Plt./238, 240
See application file for complete search history.

*Primary Examiner* — Susan McCormick Ewoldt
(74) *Attorney, Agent, or Firm* — Penny J. Aguirre

(57) ABSTRACT

A new cultivar of Azalea named 'AZ 32', that is characterized by its repeat blooming habit, its floriferous blooming habit with bright red purple single flowers with wavy petal margins, its upright plant habit, its dark green foliage that has been observed to be pest free, its high tolerance to heat and humidity when grown in Southern U.S.A, and its ability to be readily propagated by softwood stem cuttings with a high percentage of successful rooting and a vigorous root system.

2 Drawing Sheets

Botanical classification: *Rhododendron hybrida.*
Cultivar designation: 'AZ 32'.

BACKGROUND OF THE INVENTION

The present invention relates to a new and distinct cultivar of *Rhododendron* plant of hybrid origin, botanically known as *Rhododendron hybrida* 'AZ 32' and will be referred to hereafter by its cultivar name, 'AZ 32'. 'AZ 32' is a new cultivar of evergreen Azalea grown for use as a landscape plant.

The new cultivar was developed through an on-going breeding program conducted by the Inventors in Poplarville, Miss. The objectives of the breeding program are to develop new cultivars of Azalea that exhibit tolerance to environmental stresses and disease resistance combined with unique flower colors and extended bloom periods.

The new cultivar arose from a cross made in spring of 2005 between an unnamed plant received from a breeding program in Semmes, Ala., Ref. No. TD28, as the female parent, and 'Red Slippers' (not patented) as the male parent. The Inventors selected 'AZ 32' as a single unique plant amongst the seedlings that resulted from the above cross in 2007.

Asexual propagation of the new cultivar was first accomplished by softwood stem cuttings in Poplarville, Miss. in 2008 by one of the Inventors. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics 'AZ 32'. These attributes in combination distinguish 'AZ 32' as a new and distinct cultivar of Azalea.

1. 'AZ 32' is a repeat bloomer with a strong bloom period in late March to early April followed by a seconding bloom period in late July through October in Mississippi.
2. 'AZ 32' exhibits a floriferous blooming habit with bright red purple single flowers with wavy petal margins.
3. 'AZ 32' exhibits an upright growth habit suitable for smaller landscapes.
4. 'AZ 32' exhibits dark green foliage that has been observed to be pest free.
5. 'AZ 32' exhibits a high tolerance to heat and humidity when grown in Southern U.S.A.
6. 'AZ 32' is readily propagated by softwood stem cuttings; with a high percentage of successful rooting and a vigorous root system.

The female parent of 'AZ 47', Ref. No. TD28, differs from 'AZ 32' in having winter foliage that thins, in being less floriferous, and in having lighter pink flowers. The male parent, 'Red Slippers', differs from 'AZ 32' in having less cold hardiness, in blooming earlier resulting in susceptibility to frost damage to its flowers, and in having a weaker root system. 'AZ 32' can also be most closely compared to the cultivars 'Southern Summer Sun' (not patented), 'AZ 47' (U.S. patent application Ser. No. 13/987,581) and 'RLH1-3P3' (U.S. Plant Pat. No. 21,512). ALL are similar to 'AZ 32' in having repeat blooming habits with 'Southern Summer Sun' also similar in heat tolerance. 'RLH1-3P3' differs from 'AZ 32' in having less tolerance to heat and full sun, in having poor tolerance to rain and humidity during spring flowering, and in having white flowers. 'AZ 47' differs from 'AZ 32' in having flowers that are duller red-purple in color with petal margins that are less wavy. 'Southern Summer Sun' differs from 'AZ 32' in being more difficult to propagate, in having less cold hardiness, and in having a more open growth habit.

BRIEF DESCRIPTION OF THE DRAWINGS

The accompanying colored photograph illustrates the overall appearance and distinct characteristics of the new Azalea. The photographs were taken of three year-old plants of 'AZ 32' as grown outdoors in a three-gallon container in Grand Saline, Tex.

The photograph in FIG. 1 provides a view of 'AZ 32' in bloom.

Figure 1:
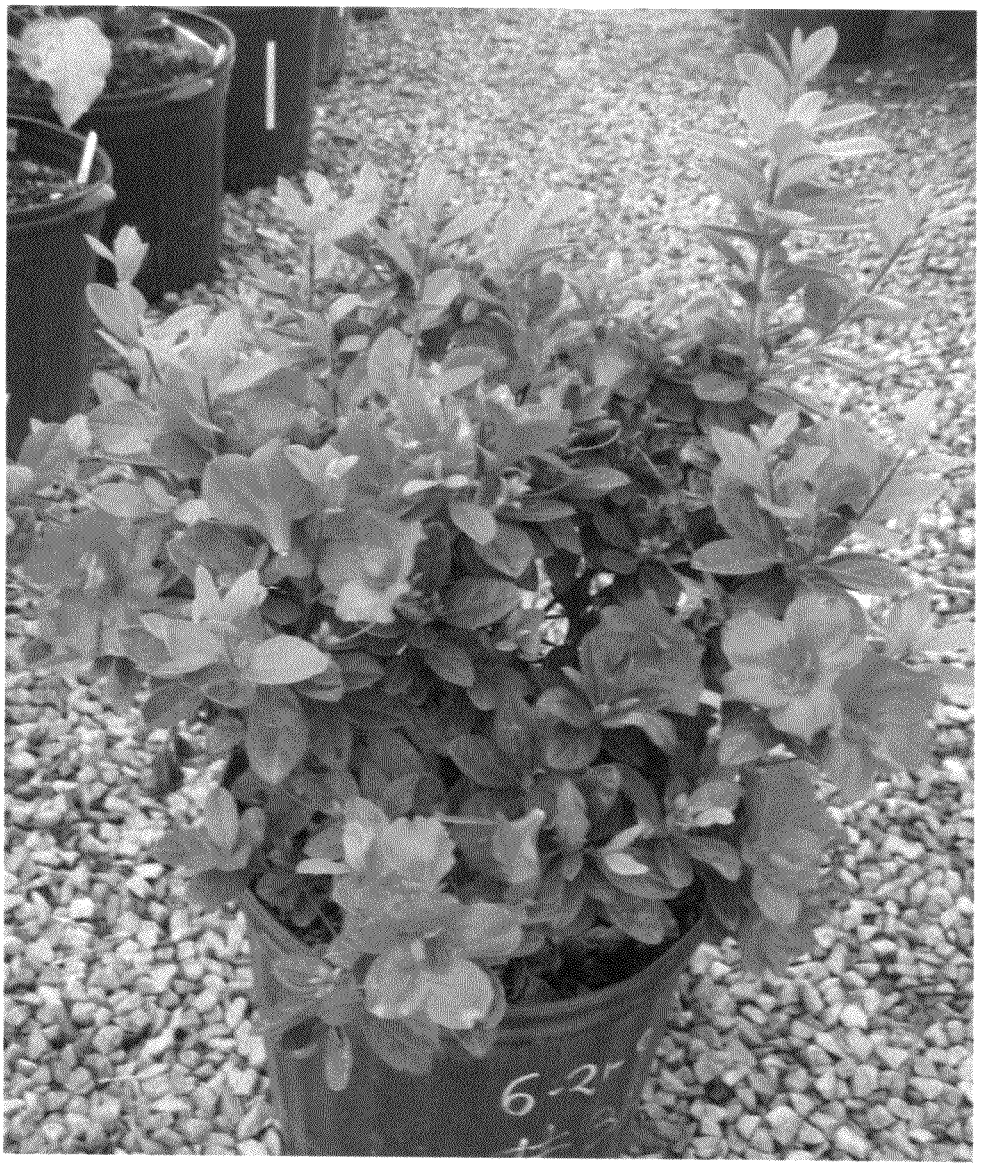
Figure 2:
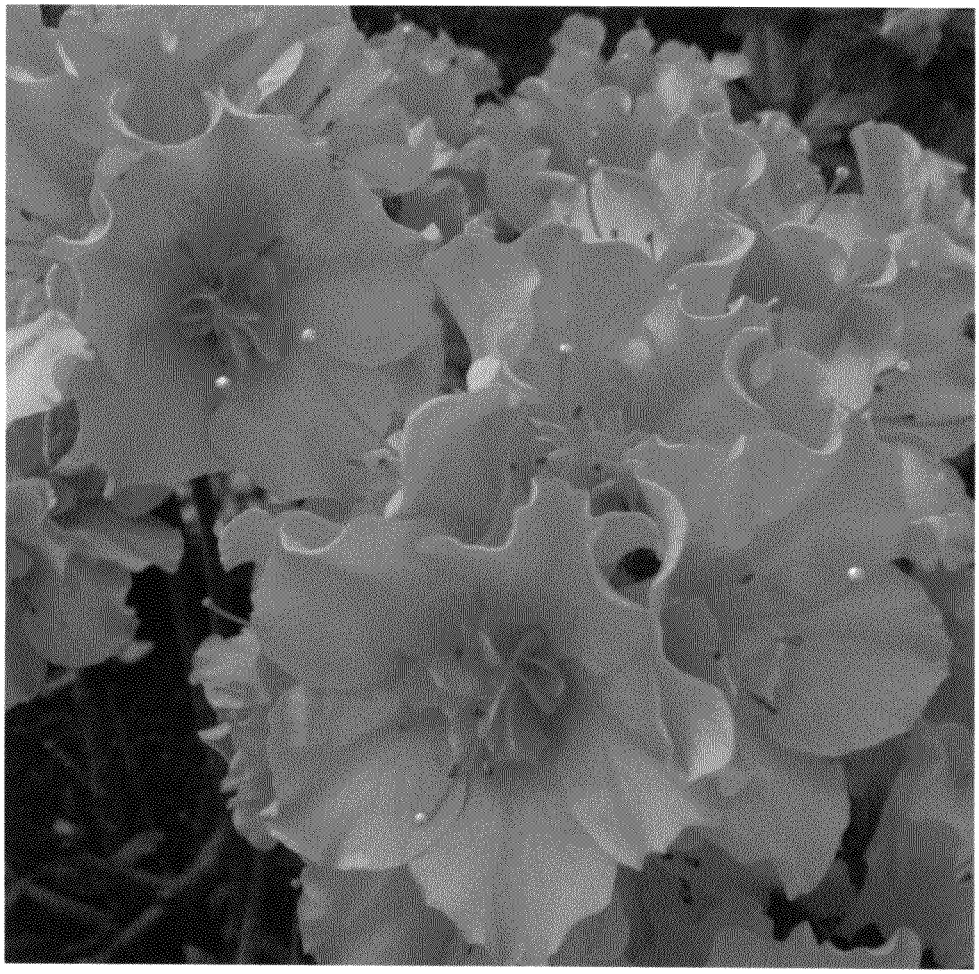

The photograph in FIG. 2 provides a close-up view of the inflorescences of 'AZ 32'.

The colors in the photographs are as close as possible with the digital photography and printing techniques utilized and the color codes in the detailed botanical description accurately describe the new Azalea.

DETAILED BOTANICAL DESCRIPTION OF THE PLANT

The following is a detailed description of 18 month-old plants of the new cultivar as grown outdoors in three-gallon containers in a greenhouse in Grand Saline, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—Late March to early April and repeats in late July to October in Southern Mississippi, USA.

*Plant type.*—Evergreen shrub.

*Plant habit.*—Upright and compact.

*Height and spread.*—Reaches about 30 cm in height and 40 cm in spread as grown in a 3-gallon container.

*Hardiness.*—Cold hardiness. — At least in U.S.D.A. Zones 7.

*Diseases.*—Resistance to common azalea pests is equivalent or better than commonly planted azalea clones.

*Pests.*—Foliage has been observed to be pest free under the conditions grown.

*Environmental conditions.*—Has been observed to be highly tolerant to high heat and humidity in southern U.S.A.

Root description: Abundant, fibrous, moderately dense.

*Propagation.*—Softwood stem cuttings under mist.

*Growth rate.*—Vigorous.

Stem description:

*Shape.*—Round.

*Stem color.*—New growth; 145C with markings and hairs of 175A, mature wood; a blend of 200A and 200B.

*Stem size.*—Main stems; an average of 8 cm in length and 1.5 cm in width, lateral stems; an average of 20 cm in length and 3 mm in diameter.

*Stem surface.*—New growth; very pubescent, mature wood; ridged bark, exfoliating.

*Stem aspect.*—Held upright at an average angle of 15° (0°=vertical).

*Stem strength.*—Strong.

*Branching.*—Densely-branched, an average of 30 lateral branches in a 3-gallon container.

*Internode.*—Average of 1.5 cm in mid range of lateral branches.

Foliage description:

*Leaf shape.*—Oblanceolate.

*Leaf division.*—Simple.

*Leaf base.*—Cuneate.

*Leaf apex.*—Mucronate.

*Leaf venation.*—Pinnate, upper and lower surface; 145C in color, upper surface moderately covered with stiff pubescence, 1 mm in length and matches vein color, lower surface pubescence N34A in color.

*Leaf margins.*—Entire.

*Leaf attachment.*—Petiolate.

*Leaf arrangement.*—Alternate.

*Leaf orientation.*—Held horizontal to upright.

*Leaf aspect.*—Cupped downward.

*Leaf surface.*—Upper and lower surface coriaceous, cartilaginous, and shiny.

*Leaf color.*—Young leaves upper and lower surface; 144A, mature leaves upper surface; 133A, mature leaves lower surface; 146C.

*Leaf size.*—Average of 4 cm in length, and 1.5 cm in width.

*Leaf quantity.*—About 20 leaves per lateral branch 20 cm in length.

*Petioles.*—Average of 5 mm in length and 1 mm in diameter, 145B in color, sparsely pubescent surface.

Flower description:

*Inflorescence type.*—Flowers are solitary.

*Lastingness of flowers.*—About 10 days, self cleaning.

*Flower size.*—An average of 4 cm in depth and 5.5 cm in diameter.

*Flower fragrance.*—None.

*Flower shape.*—Tubular base with flared petal lobes.

*Flower number.*—Average of 3 per lateral stem.

*Flower aspect.*—Upright.

*Flower bud.*—Ovate in shape, an average of 2.5 cm in length and 1.2 cm in diameter, acute apex, color; a blend of 63A and 63B with sepal portion 144A.

*Flower attachment.*—Pedicel.

*Petal number.*—5.

*Petal shape.*—Spatulate with base fused and upper lobe orbicular.

*Petal aspect.*—About 30% fused into tube with lobes flared and slightly overlapping.

*Petal color.*—N57A with undertones of N57C in full sun, internal freckles 60A in color.

*Petal surface.*—Both surfaces glabrous.

*Petal margins.*—Wavy.

*Petal apex.*—Rounded.

*Petal base.*—Fused.

*Petal size.*—Average of 4 cm in length and 2.3 cm in width.

*Petaloids.*—An average of 5, spathulate and distorted in shape and wrapped around stamen filaments, arrange from 0.4 to 2.8 cm in length and 0.3 to 0.8 mm in width, color matched petal color, undulating margins, rounded apex and narrow acuminate base.

*Sepal number.*—5.

*Sepal shape.*—Lanceolate.

*Sepal margin.*—Entire.

*Sepal size.*—Average of 1 cm in length and 3 mm in width.

*Sepal aspect.*—Upright.

*Sepal surface.*—Pubescent on both surfaces.

*Sepal apex.*—Acute-slightly acuminate.

*Sepal base.*—Fused.

*Sepal color.*—Center 144A suffused with 35B in center and at base of upper and lower surface.

*Calyx.*—Campanulate in shape, average of 1 cm in length and 1.5 cm in diameter.

*Peduncles.*—An average of 1.1 cm in length and 2 mm in diameter, pubescent surface, 58A in color.

*Pedicels.*—None.

*Bracts.*—Average of 3 at base of flower or pair, wedge-shaped and cupped inward and occasionally with leaf-like tip, about 1.6 cm in length and 0.9 cm in width, a blend of 145A, 145B, and 145C in color, base cuneate, apex blunt to having a small leaf tip, glabrous on both surfaces.

Reproductive organs:

*Gynoecium.*—1 Pistil, stigma; club-shaped, about 1 mm in diameter and 61A in color, style; 2.5 cm in length, 1 mm in width and 66B in color, ovary; conical in shape, 4 mm in length and 3 mm in width, 155A in color due to heavy pubescence.

*Androecium.*—Stamens; average of 5, surrounded petaloids with just the upper 5 mm extending beyond, filament; average of 2 cm in length, N66B in color, anthers; a blend of N186B and N186C in color; pollen sparse in quantity and N155A in color.

*Fruit/seeds.*—Seed pod an average of 15 mm in length and 5 mm in width, matures from 139C to 200B in color.

It is claimed:

1. A new and distinct cultivar of Azalea plant named 'AZ 32' as herein illustrated and described.

* * * * *